(12) United States Patent
Britva et al.

(10) Patent No.: US 10,238,849 B2
(45) Date of Patent: Mar. 26, 2019

(54) SONOTRODE

(75) Inventors: Alexander Britva, Migdal Ha'emek (IL); Alexander Dverin, Netanya (IL); Yevgeny Pens, Haifa (IL); Ziv Karni, Kfar Shmaryahu (IL)

(73) Assignee: Alma Lasers Ltd.

( * ) Notice: Subject to any disclaimer, the term of this patent is extended or adjusted under 35 U.S.C. 154(b) by 143 days.

(21) Appl. No.: 13/386,949

(22) PCT Filed: Jul. 30, 2010

(86) PCT No.: PCT/IB2010/053474
§ 371 (c)(1),
(2), (4) Date: Jan. 25, 2012

(87) PCT Pub. No.: WO2011/013101
PCT Pub. Date: Feb. 3, 2011

(65) Prior Publication Data
US 2012/0123319 A1 May 17, 2012

Related U.S. Application Data

(60) Provisional application No. 61/229,817, filed on Jul. 30, 2009.

(51) Int. Cl.
*A61M 37/00* (2006.01)
*A61B 17/00* (2006.01)

(52) U.S. Cl.
CPC .......... *A61M 37/0092* (2013.01); *A61B 2017/00765* (2013.01)

(58) Field of Classification Search
CPC ...... A61M 2038/0007; A61M 37/0092; A61M 2210/0612; A61M 2205/058; A61M 2205/3693; A61M 2037/0007; A61M 2205/3375; A61F 9/00736; A61F 9/00745; A61F 17/320068; A61F 2017/320084;
(Continued)

(56) References Cited

U.S. PATENT DOCUMENTS 3,792,701 A * 2/1974 Kloz ................. A61B 1/12
600/104
4,612,809 A * 9/1986 Cribbs ............... G01N 29/262
600/437
(Continued)

FOREIGN PATENT DOCUMENTS

JP   2000233006   8/2000
JP   2001512329   8/2001
(Continued)

OTHER PUBLICATIONS

PCT Search report of PCT/IB10/53474 dated Oct. 20, 2010 by European Patent Office Rijswijk, NL.
(Continued)

*Primary Examiner* — Bradley J Osinski
*Assistant Examiner* — Laura Schell

(57) ABSTRACT

Disclosed are a sonotrode and its use for transdermal delivery of therapeutic or cosmetic compounds. The sonotrode 10 comprises a tubular neck 14 attached at a proximal end to a solid head 12 and ending at a distal end in a flared foot 16. When coupled to an ultrasonic transducer and applied to skin of a human or animal, the sonotrode enhances the delivery of compounds into the skin.

15 Claims, 3 Drawing Sheets

(58) Field of Classification Search
CPC .... A61N 2007/0034; A61N 2007/0065; A61N 7/00; A61B 2017/320072; A61B 2017/320076; A61B 2017/320004; A61B 2017/320008; A61B 2017/320012
USPC .......................................................... 604/22
See application file for complete search history.

(56) References Cited

U.S. PATENT DOCUMENTS

| | | | | |
|---|---|---|---|---|
| 5,527,273 | A * | 6/1996 | Manna | A61B 17/22012 604/22 |
| 5,725,495 | A * | 3/1998 | Strukel | A61M 1/0035 604/22 |
| 6,322,532 | B1 | 11/2001 | D'Sa et al. | |
| 6,575,956 | B1 | 6/2003 | Brisken et al. | |
| 6,648,872 | B1 * | 11/2003 | Zappala | A61B 17/1322 424/400 |
| 7,025,735 | B2 * | 4/2006 | Soring et al. | 601/2 |
| 7,737,108 | B1 | 6/2010 | Hoffman et al. | |
| 2003/0078499 | A1 | 4/2003 | Eppstein | |
| 2003/0130575 | A1 * | 7/2003 | Desai | A61B 8/0841 600/417 |
| 2004/0210184 | A1 | 10/2004 | Kost et al. | |
| 2007/0299369 | A1 * | 12/2007 | Babaev | A61M 1/0088 601/2 |
| 2008/0097253 | A1 * | 4/2008 | Pedersen | A61B 8/546 601/2 |
| 2008/0183167 | A1 * | 7/2008 | Britva | A61B 18/042 606/41 |
| 2009/0155199 | A1 | 6/2009 | Babaev | |
| 2011/0213279 | A1 | 9/2011 | Britva et al. | |

FOREIGN PATENT DOCUMENTS

| | | |
|---|---|---|
| JP | 2002515786 | 5/2002 |
| JP | 2004277325 | 10/2004 |
| JP | 2006527008 | 11/2006 |
| JP | 2009190789 | 8/2009 |
| WO | 1998000194 | 1/1998 |
| WO | 1998029134 | 7/1998 |
| WO | 2000021605 | 4/2000 |
| WO | WO2000021605 | 4/2000 |
| WO | 2005004972 | 1/2005 |
| WO | 2007136909 | 11/2007 |
| WO | WO2009095894 | 8/2009 |

OTHER PUBLICATIONS

PCT search opinion of PCT/IB10/53474 dated Oct. 20, 2010 by European Patent Office Rijswijk, NL.
Letter accompanying ammended claims of PCT/IB10/53474, faxed from Bushy Heath, United Kingdom dated Nov. 19, 2010.
In corresponding EP application No. EP20100745012, granted as patent EP2459268: office action of Nov. 6, 2012 and response thereto (starts on p. 5).
In corresponding CN application No. CN201080033374.3 granted as patent CN102438695: office action of Apr. 28, 2013 (in translation), citing WO 00/21605 (of. ISR), and response thereto (starts on p. 9).
In corresponding JP application No. JP2012-522330, granted as patent JP5503741: office action of Oct. 15, 2013 (in translation) citing various references and response thereto (starts on p. 5). References cited in the action are listed separately in this IDS.
In corresponding JP application No. JP2012-522330, granted as patent JP5503741: office action of Oct. 15, 2013 (in translation) citing various references and response thereto (starts on p. 5). References cited in the action are listed in order in the foreign patents section of this IDS.

\* cited by examiner

SONOTRODE

RELATED APPLICATION

The present application is based on and claims priority from U.S. provisional application No. 61/229,817 which was filed on 30 Jul. 2009 and is herein incorporated by reference in its entirety

FIELD OF THE INVENTION

The present invention relates to apparatus and methods for delivery of substances through substrates and, more particularly, to apparatus and methods for using ultrasound to enhance transdermal delivery of drugs or cosmetics. In particular, the present invention relates to sonotrodes and their use in the transdermal delivery of medicaments.

BACKGROUND OF THE INVENTION

The skin is one of the most readily accessible organs of the human body, covering a surface area of approximately 2 $m^2$ and receiving about one third of the body's blood circulation. The skin is a complex system consisting of the epidermis, the dermis, and skin appendages, such as hairs, interwoven within the two layers. The outermost layer of the skin, the epidermis, is avascular, receiving nutrients from the underlying dermal capillaries by diffusion through a basement membrane. The outermost layer of the epidermis is called the stratum corneum, the protective covering that serves as a barrier to prevent desiccation of the underlying tissues and to exclude the entry of noxious substances from the environment, including agents applied to the skin. This layer consists of corneocytes embedded in lipid regions.

Transdermal (or transcutaneous) drug delivery offers advantages over traditional drug delivery methods, such as injections and oral delivery. In particular, transdermal drug delivery avoids gastrointestinal drug metabolism, reduces side-effects and can provide sustained release of therapeutic compounds. The term "transdermal" is used generically because, in reality, transport of compounds by passive diffusion occurs only across the epidermis where absorption into the blood via capillaries occurs.

However, the diffusion rate of topically applied compounds will vary because of both internal (physiological) and external (environmental) factors. The diffusion rate is also dependent upon physical and chemical properties of the compounds being delivered. The patient's skin needs to be carefully evaluated to minimize the natural, internal barriers to transdermal drug delivery (e.g. dry skin, thick skin, dehydration, poor circulation, poor metabolism) and to maximize the natural enhancers (e.g. ensuring the patient is well hydrated and selecting an area of skin that is thin, warm, moist, and well perfused). The stratum corneum is considered to be the rate-limiting barrier for transdermal delivery and so diffusion is often enhanced. Various methods include preheating the skin to increase kinetic energy and dilate hair follicles, and covering the area with an occlusive dressing after the drug application to maintain moisture and activate the reservoir capacity of the skin.

Enhancers of transcutaneous drugs are usually used to alter the nature of the stratum corneum to ease diffusion. This alteration may result from denaturing the structural keratin proteins in the stratum corneum, stripping or delaminating the cornified layers of the stratum corneum, changing cell permeability, or altering the lipid-enriched intercellular structure between corneocytes. Enhancers are incorporated into transdermal-controlled drug delivery systems, or they are used prior to, during, or after the topical application of a drug. Preferred enhancers allow drugs to diffuse actively and quickly, but do not inactivate the drug molecules, damage healthy epidermis, cause pain, or have toxicological side effects.

Even though ultrasound has been used extensively for medical diagnostics and physical therapy, it has only recently become popular as an enhancer of drug delivery. Numerous studies have demonstrated that ultrasound is generally safe, with no negative long-term or short-term side effects, but the mechanisms by which ultrasound works as an enhancer are less clearly understood.

Ultrasound is defined as sound at a frequency of between 20 kHz and 10 MHz. The properties defining the ultrasound are the amplitude and the frequency of the sound waves. Similar to audible sound, ultrasound waves undergo reflection, refraction, or absorption when they encounter another medium with dissimilar properties. If the properties of the encountered medium are different from those of the transmitting medium, the acoustic energy of the transmitted ultrasound beam is attenuated by being absorbed or dissipated. Attenuation of ultrasound in tissue limits its depth of penetration.

Both the thermal and non-thermal characteristics of high-frequency sound waves can enhance the diffusion of topically applied drugs. Heating from ultrasound increases the kinetic energy of the molecules (mobility) in the drug and in the cell membrane, dilates points of entry such as the hair follicles and the sweat glands, and increases the circulation to the treated area. These physiological changes enhance the opportunity for drug molecules to diffuse through the stratum corneum and be collected by the capillary network in the dermis. Both the thermal and non-thermal effects of ultrasound increase cell permeability. The mechanical characteristics of the sound wave also enhance drug diffusion by oscillating the cells at high speed, changing the resting potential of the cell membrane and potentially disrupting the cell membrane of some of the cells in the area.

One of the theories of ultrasound phoresis postulates that the main factor is increasing the permeability of a skin by creating lipid bridges between keratin layers in stratum corneum.

Another important factor that may affect drug diffusion is related to the shear forces (or shock waves) that occur when adjacent portions of the same membranous structures vibrate with different displacement amplitudes. The acoustic waves cause streaming and/or cavitation in the drug medium and the skin layers, which helps the drug molecules to diffuse into and through the skin. "Streaming" is essentially oscillation in a liquid that forces the liquid away from the source of the energy, while "cavitation" is the formation of bubbles in a liquid that is subjected to intense vibration. Cavitation is the result of rarefaction areas during propagation of longitudinal acoustic waves in the liquid when the waves have an amplitude above a certain threshold.

When these bubbles occur in specific cells of the skin, fatigue or rupture of the cells can occur as the bubbles reach an unstable size. Destruction of cells in the transmission path of the ultrasound may facilitate intercellular diffusion of drug molecules. Cavitation may also destruct the organization of lipids in the stratum corneum, resulting in an increase in the distance between the lipid layers. As a result, the amount of waster phase in the stratum corneum increases thereby enhancing the diffusion of water-soluble components through the intercellular space (Mitragotri et al (1995) J. Pharm Sci. 84: 697-706). As the permeation pathway for topically applied products is mainly along the tortuous intercellular route, the lipids in the stratum corneum play a crucial role in proper skin barrier function.

The use of ultrasound to enhance the transport of a substance through a liquid medium is referred to as sonophoresis or phonophoresis. It may be used alone or in combination with other enhancers, such as chemical enhancers, iontophoresis, electroporation, magnetic force fields, electromagnetic forces, mechanical pressure fields or electrical fields.

Ultrasound is applied via a sonotrode, also termed an acoustic horn. The sonotrode serves various functions such as conversion of the acoustic waves, by increasing the amplitude of the oscillations, modifying the distribution and matching acoustic impedance to that of the substrate. Resonance of the sonotrode, which increases the amplitude of the acoustic wave, occurs at a frequency determined by the characteristics of modulus elasticity and density of the material from which the sonotrode is made, the speed of sound through the material and the ultrasonic frequency. The size and shape (round, square, profiled) of a sonotrode will depend on the quantity of vibratory energy and a physical requirements for each specific application.

The use of sonophoresis to enhance the transdermal delivery of medicaments is known and described in various patent documents, including U.S. Pat. No. 6,322,532, U.S. Pat. No. 6,575,956, U.S. Pat. No. 7,737,108, US 2004/210184 and US 2009/155199.

There is an ongoing need for improved devices and methods to enhance transdermal medical and cosmetic compound delivery. In particular, there is an ongoing need for ultrasound-based devices and techniques for transdermal drug or cosmetic delivery.

The most popular sonotrode is a linear taper as shown in FIG. 1 of the accompanying drawings. This shape is simple to make but its potential magnification is limited to a factor of approximately four-fold. The variation of the amplitude of vibration along the length of the sonotrode for this shape is shown in FIG. 1*a*.

An alternative design employs an exponential taper as shown in FIG. 2. The amplitude of vibration for this shape of sonotrode is shown in FIG. 2*a*. This design offers higher magnification factors than a linear taper but its curved shape is more difficult to make. However, its length, coupled with a small diameter at the working end makes this design particularly suited to micro applications.

It is also known to use a stepped design as shown in FIG. 3, in which there is an abrupt transition from the diameter of the proximal portion coupled to the sound generator and the distal portion applied to the substrate. The variation of amplitude for this shape of sonotrode is shown in FIG. 3*a*. In this stepped design, the magnification factor is given by the ratio of the end areas and the potential magnification is limited only by the dynamic tensile strength of the sonotrode material. This is a useful design and easy to manufacture, while gains of up to 16-fold are easily achieved.

Sonotrodes connected to ultrasound transducers, especially those employed for transdermal delivery of drugs, typically have a length L, expressed by the equation $L=n(\lambda/2)$, where $\lambda$ is the wavelength of the ultrasound in the sonotrode and n is a positive integer. In this case, the maximum amplitudes of the acoustic wave are found at the proximal end of the sonotrode and at the $\lambda/2$ length beyond the foot of the sonotrode.

Burning and abrasion of the epidermis is also a serious consideration when using ultrasound. Ultrasound should act as a mechanical pressure agent without destructing the epidermis of the skin. However, cavitation in the liquid coupling the sonotrode to the skin may produce cavitation erosion of the epidermis and the dermis. While this cavitation assists with active penetration of the substance being delivered, such cavitation may also destruct the epidermis.

A further challenge when using ultrasound is that it is low in efficiency due to cavitation in the buffer suspension and the low acoustic pressure and ultrasonic energy that is required to prevent burning and other injury.

SUMMARY OF THE INVENTION

With a view to mitigating the drawbacks and limitations of the known technology, the present invention provides in its broadest aspect a sonotrode for use in transdermal delivery of therapeutic or cosmetic compounds, the sonotrode comprising a proximal portion to be coupled in use to an ultrasound generator, a neck portion coupled at one end to the proximal portion and terminating at a distal end in a flared foot portion, the neck portion having a smaller cross sectional area than both the foot portion and the proximal portion, and the distal end of the sonotrode being formed with a blind bore that passes through the flared foot portion and extends into the neck portion.

In essence, the end of the sonotrode resembles the horn of a trumpet, being tubular with a flared distal end.

Preferably, both the proximal portion and the neck portion are cylindrical with a constant outer diameter and the blind bore is a cylindrical bore with parallel sides and extends over substantially the whole length of the neck portion.

A sonotrode of this shape may be used to facilitate the transdermal delivery of compounds, either therapeutic or cosmetic. Since there will always be an element of passive diffusion, the sonotrode of the invention provides an additional force, in the form of ultrasound, that pushes the compound or compounds through the stratum corneum, the outer layer of the skin.

Prior to the application of ultrasound, the skin is preferably treated to form a series of perforations in the stratum corneum. Such perforation can be carried out mechanically, such as by small needles on a cylinder that is rolled over the skin area to be treated. It is preferred however for the perforations to be burnt into the skin, as can be achieved by use of a laser or using RF energy. $CO_2$ lasers and Er:YAG-lasers are preferred.

It is believed that the vibrating column of air within the blind bore in the distal end of the sonotrode of the present invention together with the vibration of the annular end surface of the foot portion has the effect of cyclically reducing and increasing the pressure at the skin interface and that this sucking and blowing action is effective in transporting the compound to be delivered through the perforations in the stratum corneum.

Preferably, the sonotrode has a total effective length that is substantially equal to one third of the wavelength $\lambda$ of the ultrasound in the sonotrode. In this context, "substantially equal" means within about 5% of this value and the term "effective length" is intended to include harmonically related lengths, i.e. lengths that differ from $\lambda/3$ by a whole number of half wavelengths.

By selecting the length of the sonotrode in this manner, when coupled to the skin of a patient maximum acoustic wave amplitude is achieved not at the interface with the skin but at some distance below the surface of the skin. It will be appreciated that increasing the length of the sonotrode by multiples of $\lambda/2$ does not affect the phase of the ultrasound at the interface between the sonotrode and the skin and does not change the way in which the ultrasound can penetrate beneath the skin. It is for this reason that harmonically related lengths may alternatively be employed.

The ultrasonic acoustic waves emitted by the flared foot of the sonotrode are believed to assist in spreading through the dermis the compound that has been transported through the perforated stratum corneum and the flaring of the foot serves to spread the ultrasonic waves over a greater area to assist in diffusion of the compound.

Preferably, the length of the proximal portion is substantially the same as the length of the neck and foot portions combined. For example, the head and neck portions may each have an effective length of $\lambda/6$ where $\lambda$ is the wavelength of the ultrasound in the sonotrode.

The product of the frequency of the ultrasonic vibrations and the wavelength is equal to the speed of sound through the material of the sonotrode. For this reason, the physical length of the sonotrode will in practice depend on the material from which the sonotrode is made.

In a preferred embodiment, the diameter of the proximal portion is approximately two or three times the external diameter of the neck.

The ratio between the internal and outer diameters of the neck may be at least one quarter (1:4) or one third (1:3) and more preferably at least one half (1:2). If this ratio is too high, the walls of neck may not be thick enough to be durable but if the ratio is too small, the stress on neck may be insufficient, as explained below, to achieve the functionality desired for the sonotrode.

In an embodiment of the invention, the internal diameter is between 50% and 80% of the external diameter of the neck. The thickness of the wall of the neck may be between about 1% and 10% of the length of the neck. For a sonotrode made of aluminium, a particularly suitable wall thickness is between about 1 to 2 mm.

Preferably, the neck is circular in cross section. It is advantageous if the blind bore in the neck is also circular in cross-section.

The ratio between the diameter of the foot and the outer diameter of the neck may be at least about 3:2. Gradual flaring of the foot instead of an abrupt transition is believed to be useful for the mechanical durability and for smooth transmission of ultrasound.

Ideally, the flared foot has a substantially flat lower surface. This enables a strong seal to be made between the base of the foot and the skin surface. It also ensures that irregularities in the under surface of the foot do not affect the resonance frequency of the sonotrode.

It is advantageous for the sonotrode to be formed of a material having a characteristic impedance matching as closely as possible that of the body. Hence, it is preferred for the sonotrode to be made of aluminium or an aluminium alloy but alternative materials include alumina, titanium, stainless steel, steel, iron, plastics, or glass, either alone or in combination.

In operation, the ultrasound transducer generates longitudinal acoustic waves of wavelength $\lambda$ which are received by the sonotrode. The foot of the sonotrode acts as an energy output surface and transmits the acoustic waves to a substrate, in this case skin of a human or animal.

While ultrasound may be used to enhance transdermal delivery of one or more compounds on its own, it is sometimes desirable to use additional enhancers to enhance the delivery further. Suitable enhancers include chemical enhancers, such as creams, emulsions, suspensions and gels.

In another aspect, the present invention encompasses the use of ultrasound, in combination with electromagnetic radiation, for the transdermal delivery of at least one therapeutic or cosmetic compound. Suitable electromagnetic radiation includes laser light and radio waves. The electromagnetic radiation may be applied before or during the ultrasound.

In a further aspect, the present invention resides in a method for transdermal delivery of one or more therapeutic or cosmetic compounds, the method comprising dermal application of ultrasound via a sonotrode as described above when coupled to an ultrasound transducer.

The ultrasound transducer may either have a fixed frequency to suit the length of the sonotrode or it may be tunable to a frequency at which the sonotrode resonates when applied to skin of a human or animal.

Preferably, the ultrasound is tuned so the ultrasound waves reach maximum intensity between 0.3 mm and 2.0 mm, preferably between about 1.0 mm and 2.0 mm, below the outer surface of the skin.

A suitable operating frequency for the sonotrode is between about 26.7 kHz and 27.3 kHz. This frequency range has been found to be sufficient to induce cavitation of the skin and enhance transport.

Ultrasound may be generated either continuously or as a series of pulses. The average fluence (i.e. energy flow per unit area) should not be so high as to raise the skin temperature by more than about 1° C. to 2° C.

BRIEF DESCRIPTION OF THE DRAWINGS

The invention will now be described further, by way of example, with reference to the accompanying drawings, in which.

DETAILED DESCRIPTION OF THE PREFERRED EMBODIMENT(S)

Figure 1:
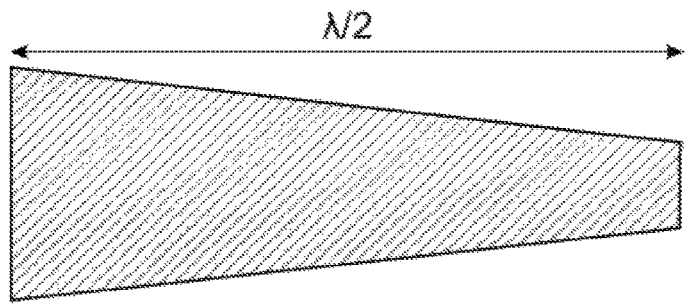
FIGS. 1, 1a, 2, 2a, 3 and 3a show, as previously described, sections through different commonly used sonotrodes together with graphs showing the variation of vibration amplitude along the length of the respective sonotrodes.
Figure 1A:
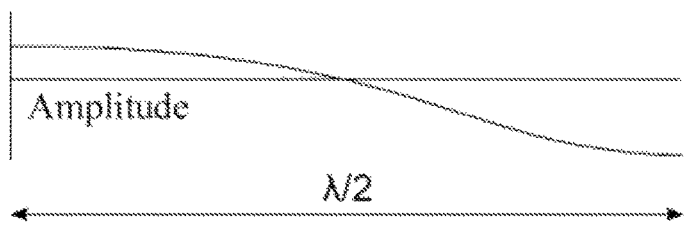
Figure 2:
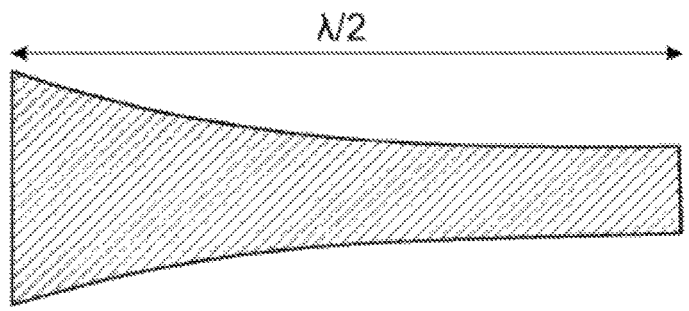
Figure 2A:
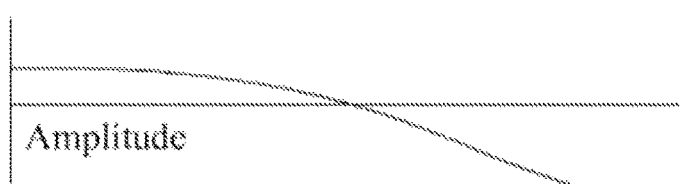
Figure 3:
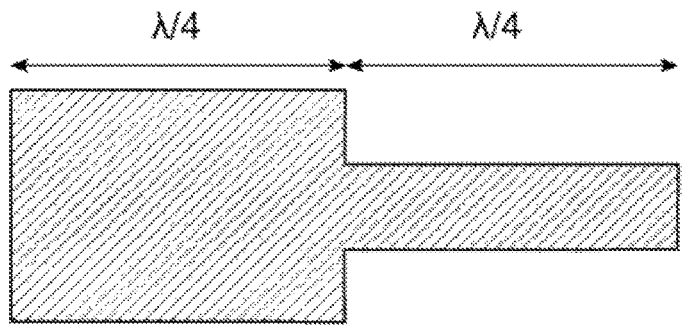
Figure 3A:
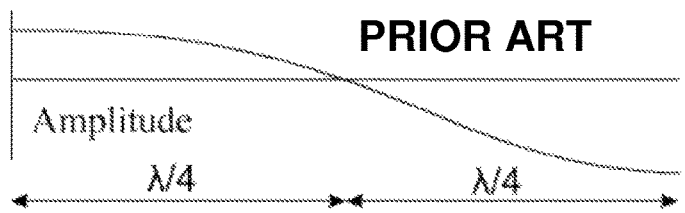
Figure 4:
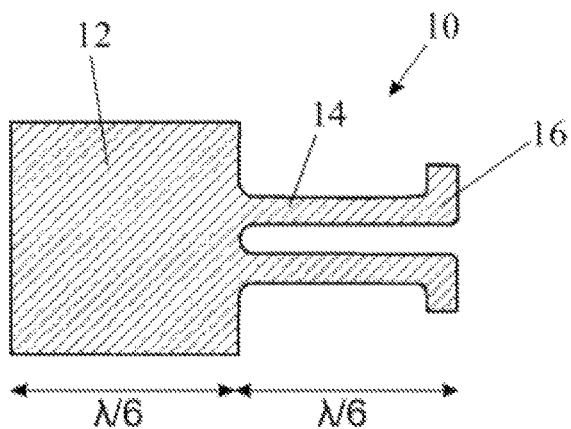
FIG. 4 is a section through a sonotrode embodying the invention.

The sonotrode 10 of FIG. 4 has a primary use to enhance the transdermal delivery of a substance, such as a drug (medicament) or cosmetic into a substrate such as human or animal skin. The sonotrode has a proximal solid head 12 attached to a tubular neck 14 that ends at its distal end with a flared (trumpet-shaped) foot 16, forming a blind bore 15.

Figure 5:
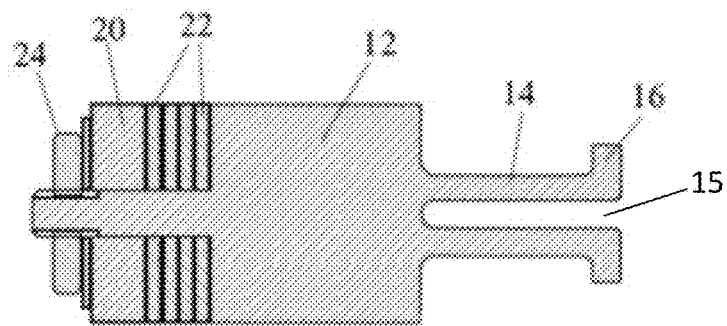
FIG. 5 shows a schematic section through the sonotrode of FIG. 4 coupled to an ultrasound generator.

The end of the head 12 is bolted in practice as shown in FIG. 5 to a mass 20, termed a back mass or gravity mass, and two pairs of piezoelectric ceramics 22 are clamped by the nut 24 between the head 12 and the back mass 20. An electrical generator is connected to conductors that apply an alternating voltage to the piezoelectric ceramics 22 to cause them to vibrate at the desired ultrasonic frequency of approximately 27.5 KHz. Though not shown in the drawing, a cooling circuit may be used to cool the sonotrode and a mechanical support is provided to grip the sonotrode in such a manner as not to dampen the ultrasonic vibrations.

Ultrasound generated by applying a voltage to the ceramics 22 enters the head 12 and propagates through the tubular neck portion 14 to the flared foot portion 16. The foot portion provides the energy output surface that delivers the ultrasound energy to the outer surface of a patient's skin.

The sonotrode shown in FIG. 4 has a total length of $\lambda/3$. Therefore, for a sonotrode of pure aluminium (in which the velocity of sound is 4.877 m/s) excited at a frequency F of 27.5 KHz, the wavelength (given by V/F) is equal to about 17.75 cm. Thus the sonotrode can have a total length of $\lambda/3$ of 5.9 cm (or a length differing from this value by $\lambda/2$, i.e. 8.875 cm).

The choice of sonotrode material is ultimately a matter of compromise. The material ideally should have the same characteristic acoustic impedance as the substrate into which the ultrasound is to be coupled (to minimise reflections at the interface) but it should have the mechanical strength to withstand the ultrasonic vibrations. The wavelength, and therefore the physical length of the sonotrode, will depend in each case on the speed of sound in the chosen material.

The head 12 of the sonotrode is solid with a circular cross-section of length $\lambda/6$. The diameter of the head will depend on the power of the sonotrode and the size of the piezoelectric ceramics. Depending on the material of the sonotrode, the length of the head portion may typically be about 40 mm and the diameter 30 mm.

The neck of the sonotrode is a hollow tube in shape, having parallel side walls. The combined length of the neck and foot portions 14 and 16 is equal to the length of the head 12. The outer diameter of the neck is typically 10 mm, its length about 35 cm and its internal diameter 6 mm. The tube thus has a wall thickness of about 2 mm.

The foot 16 is formed by a flaring of the end of the tubular neck 14. The foot 16 is circular in cross-section, has a maximum outer diameter of 15-20 mm and its axial length is about 5 mm. The outer and inner surface of the foot portion 16 flare outwards and end in a flat surface. It is this flat surface that provides the energy output surface that transmits the ultrasound into the skin.

Though other ultrasound generators may be employed, the ultrasound generator shown in FIG. 5, uses a pre-stressed piezoelectric sandwich transducer as described by Neppiras E. A. (Ultrasonics International 1973 Conference Proceedings, Butterworths, Borough Green, UK). To enhance the peak power of the transducer for drug delivery, four piezoceramic elements switched in parallel electrically and in series acoustically were used. However, two elements may also be used, as well as different configurations of the two or four elements. As an alternative, a magnetostrictive-type ultrasound transducer or any other suitable transducer for producing ultrasound energy at one or more frequencies may be used.

Ultrasound transducers typically produce 10-50 Watts of acoustic power and operate at a frequency of 20-60 kHz. However, a transducer having a real acoustic power of up to 100 Watts may be used in the present invention. The power irradiated into biological tissue will depend on the sonotrode material. For example, for an aluminium sonotrode, the power irradiated into biological tissue may be 30-50 Watts for an energy delivery surface (foot) of 0.5-5 $cm^2$. For a titanium sonotrode, the power may be 20-30 Watts for a similarly sized foot.

Since the transducer is operated at a resonant frequency, a control sub-system may be provided to tune the excitation frequency to the resonance frequency of the sonotrode.

In operation, the ultrasound transducer may be excited at a plurality of candidate frequencies. For each candidate frequency, a respective indication of the power of ultrasound waves produced by ultrasound transducer is determined. It is to be assumed that the candidate frequency associated with a local maximum of ultrasound wave power (i.e. local maximum with respect to frequency) is closest to the resonance frequency. Thus, in accordance with the power indications, an operating frequency of transducer may then be selected.

The power of ultrasound waves produced by the ultrasound transducer may be deduced from the power or current consumption of the generator. Thus the apparatus may include a current meter. In addition, one or more measuring transducers (not shown) may be associated with the sonotrode to measure the intensity of ultrasound vibrations or waves propagating within the sonotrode.

The ultrasound transducer is activated at the selected candidate frequency in a pulsed mode for a desired length of time. As the resonant frequency may drift during an activation cycle, the excitation frequency may need to be re-tuned periodically.

In an embodiment of the invention a controller is configured to perform the following steps; namely:

i) effect a frequency scan by operating the ultrasound transducer at a plurality of different candidate frequencies and determine for each candidate frequency a respective indication of a power of ultrasound waves generated by the transducer that may be associated with the given candidate frequency;

ii) select an operating frequency from the plurality of candidate frequencies in accordance with power indications; and iii) operate the transducer at the selected frequency for at least 10 seconds.

The transducer produces high acoustic pressure which is then transmitted as resonance in the structure of the sonotrode and high air pressure in the hollow neck. The ultrasonic energy is transmitted directly into the skin via the foot of the sonotrode. The sonotrode organizes the longitudinal acoustic waves so they are delivered orthogonally to the skin surface.

When coupled together, the transducer excites the sonotrode via the proximal surface of the head in a longitudinal direction. The generated ultrasonic wave propagates in the same longitudinal direction and is partially radiated from the foot of the sonotrode. The acceptor of the ultrasonic wave is the skin on which the sonotrode is placed. Because the skin has different acoustic impedance from the sonotrode, some of the acoustic wave is reflected back up the sonotrode. For example, if the sonotrode is aluminium, only 30% of the acoustic power penetrates the biological tissue. The remaining 70% is reflected producing a standing wave having a wavelength of $\lambda/2$. Thus, the sonotrode acts as an acoustic resonator. It will be appreciated that if the sonotrode is made from other materials than aluminium, the reflection coefficient may differ from 70%.

A coupling medium, such as an emulsion, a suspension, cream, liquid etc. may be placed either on the lower surface of the foot or on the skin to facilitate transmission of the ultrasound wave from the sonotrode to the skin.

The shape of the sonotrode is believed to achieve two effects. First, the hollow neck creates a vibrating air column that blows and sucks alternately, serving to transfer the medicament through the stratum corneum. Second, the setting of the length of the sonotrode to $\lambda/3$ allows the acoustic energy to be focused to a point that is between approximately 0.3 and 2 mm beneath the surface of the skin. This positioning of the maximum acoustic wave amplitude at a point deeper in the tissue magnifies the sonophoresis effect of cavitation, lipid destruction etc. and increases absorption of the drug or cosmetic.

Figure 4A:
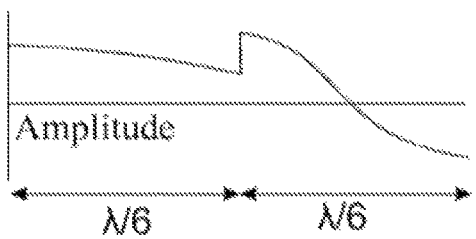
FIG. 4a shows the variation of vibration amplitude along the length of the sonotrode shown in FIG. 4.

As shown in FIG. 4a, the acoustic wave amplitude within the sonotrode, averaged over its cross section, decreases monotonically within the head of the sonotrode. At the boundary between the head and the neck, the amplitude increases strongly because of the stepping down structure of the sonotrode ($\lambda/6$ from the proximal end surface of the sonotrode head). The amplitude then decreases strongly along the neck, reaching minimum amplitude close to the middle of the neck. This point is where the distance from the proximal end surface of the sonotrode head is close to $\lambda/4$. The amplitude then increases along the remainder of the neck, reaching a high level by the time the wave is at the lower surface of the foot ($\lambda/3$ from the proximal end surface of the sonotrode head). At this point, the ultrasound is equal in amplitude but opposite in phase to the ultrasound at the junction between the neck portion 14 and the head 12.

It has been found experimentally that the sonotrode of FIG. 4 has a blowing and sucking action. This is demonstrated by a cloud that is created if the sonotrode is hovered over a power coated surface without coming into physical contact with the surface. It has also been found that the length of the sonotrode results in penetration of the ultrasound and that the maximum vibration amplitude not at the surface of the skin but at some distance below it. This is demonstrated by coupling the ultrasound into a stack of sheets of paper and increasing the energy to cause charring of the paper. It is found that sheets in contact with the sonotrode are little affected while serious charring is observed in lower sheets further spaced from the energy output surface. It is this combination of blowing and sucking with deeper penetration of the ultrasound that is believed to render the sonotrode of the preferred embodiment of this invention particularly suited to sonophoresis.

There may be other vibration modes established in the sonotrode that cause or contribute to the effects described above. A full analysis of such modes of vibration is not necessary for an understanding of the present invention, it being sufficient to recognise that that the sonotrode does result in alternating fluid pressures at the interface with the substrate and a deeper penetration of the acoustic waves.

Suction produced as a result of the pulling force may clear passageways in the skin of substances such as the drug being delivered, blood, lymph, or other biological material, (which, in the case of blood, may thereby reduce blood coagulation). In this way, the compound(s) being administered is able to penetrate more effectively into and through the skin. The suction may be particularly important for clearing passageways made in the skin if the skin has been treated prior to the ultrasound with laser, radio frequency or other methods of perforation. In such a case, the clearing of passageways that serve as tunnels through which a substance can penetrate may avoid the need to rely on diffusion as the main process of delivery of the substance via the skin. Besides clearing passageways in the skin, the suction may also be useful for mechanically pulling the skin of the patient upward into and/or towards the foot of the sonotrode or for preventing medicament from drifting or scattering away from the boundary of the sonotrode. The suction may also be effective for retrieving analytes from the skin, for example insulin for testing purposes.

The suction is believed to create very high acoustic pressure (e.g., related to an acoustic power density up to 10 Watts/cm2). The acoustic pressure may be in the form of high air pressure in a thin clearance between the skin and the foot of the sonotrode if the sonotrode is not placed in direct contact with the skin. The acoustic pressure will be in the form of high hydroacoustic pressure if a layer of liquid or gel is used to couple the foot of the sonotrode to the skin.

It should be understood that the terms "blowing" and "sucking" do not imply a gas state of matter, although the substance that may be delivered by sonotrode may be a fluid, a liquid, a powder, gel or other solid substance, or a gas. Typically, the substance is a liquid, gel or powder.

The ultrasound treatment is preferably combined with a second treatment process whereby the skin is first perforated to create a network of channels in the skin via which a compound can be delivered. This perforation is followed by ultrasonic treatment.

Figure 6:
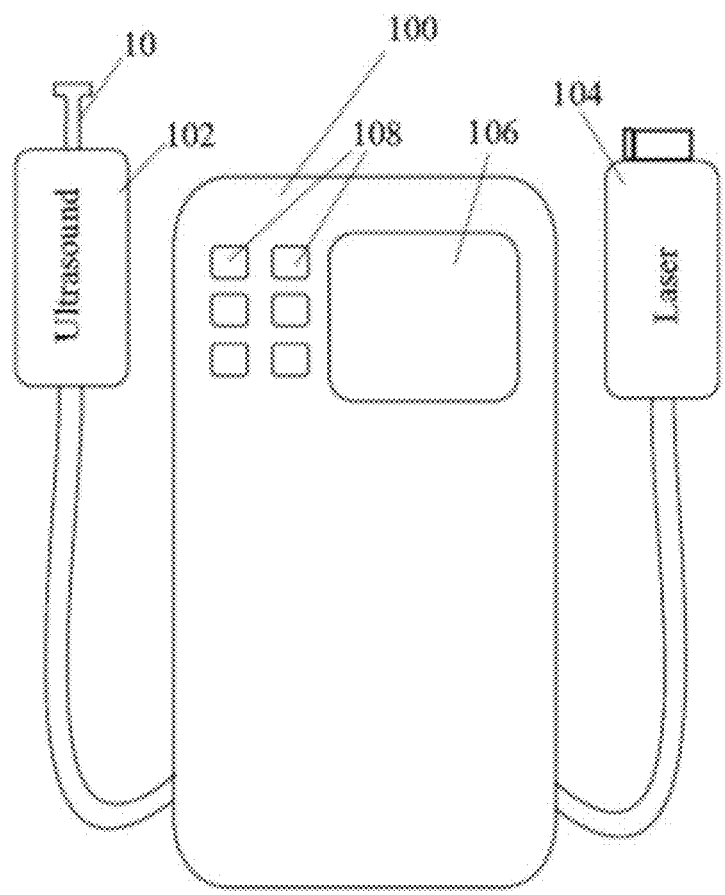
FIG. 6 is a diagram of an apparatus for transdermal delivery of a compound.

Thus the apparatus shown in FIG. 6 has a housing 100 and two applicators 102 and 104. The housing 100 contains the electronic equipment for driving the two applicators and on its front face it has various control buttons 108 and a display panel 106. The applicator 102 is used for applying ultrasound and uses a sonotrode 10 of the invention. The other applicator 104 is used to perforate the skin. The applicator 104 may comprise a series of axially spaced wheel having radially projecting spikes. The wheels are connected to an RF source within the housing 100 and sparking occurs between the spikes and the skin when the wheels are rolled over the area to be treated. The sparks burn a set and/or series of perforations passageways. Alternatively, the housing 100 may incorporate a laser, such as a fractional $CO_2$ laser, that burns a set and/or series of holes in the skin. While mechanical puncturing can also be employed, burning of the perforations has been found to enhance transdermal delivery.

The distance between the holes may be between 1 mm and 5 mm, the depth of each hole may be between 50 and 300 microns, and a grid pattern may be created. The specific values will depend upon a number of factors, for example, the skin type, age and hydration. The time between RF or laser perforation and ultrasonic treatment may be enough for lymph/blood excretion but lower than coagulation or drying time. Times of between 1 second and five minutes are contemplated.

The perforation and/or ultrasonic energy may alternatively be simultaneous, i.e. delivered from an ultrasound and a perforation device that may be moved over the surface of a patient's skin at the time so the RF or laser energy and the ultrasound energy are delivered to the patient's skin at the same time or in immediate succession. The RF applicator or ultrasound sonotrode may move or glide over the surface of the skin at a velocity that is at least 3 cm/sec (or at least 4 cm/sec, or approximately 5 cm/sec) for a period of time that is at least several seconds or at least 60 seconds.

The preliminary perforation of the skin by RF or laser is believed to be useful for increasing the permeability (transparency) of the treated skin. Delivered ultrasonic energy in the form of longitudinal waves may then induce cavitation in the stratum corneum. One or more techniques disclosed in US 2008/183167 may also be employed.

It would be possible to introduce the medicament to be delivered into the blind bore in the end of the sonotrode but more commonly the medicament may be smeared over the skin or added to the gel that is used to improve acoustic coupling.

It has been assumed in the foregoing description that the neck portion is hollow over its entire length. In practice, it is desirable for the blind bore that passes through the foot and neck portions to have a length of λ/6 but this is not essential and it is possible for part of the neck portion not to be hollow.

The invention claimed is:

1. A sonotrode for transmitting acoustic energy from an ultrasound generator to a substrate, for use in transdermal delivery of therapeutic or cosmetic compounds, the sonotrode comprising a proximal portion to be coupled in use to the ultrasound generator and a neck portion coupled at one end directly to the proximal portion and terminating at a distal end in a flared foot portion,
- acoustic energy from the ultrasound generator being applied in use to the substrate by transmission of ultrasound through the proximal portion, the neck and the foot portion,
- wherein a total effective length of the sonotrode is substantially equal to one third of a wavelength of the acoustic energy applied to the sonotrode from the ultrasound generator,
- whereby a maximum amplitude of an acoustic energy wave is focused below a surface of the skin,
- the neck portion has a smaller cross sectional area than both the foot portion and the proximal portion, and
- the distal end of the sonotrode is formed with a blind bore that opens into the flared foot portion and extends straight into the neck portion where the bore terminates.

2. The sonotrode as claimed in claim 1, wherein both the proximal portion and the neck portion are cylindrical with a constant outer diameter and the bore is a cylindrical bore with parallel sides and extends over substantially a whole length of the neck portion.

3. The sonotrode as claimed in claim 1, wherein a length of the proximal portion is substantially equal to combined lengths of the neck and foot portions.

4. The sonotrode as claimed in claim 1, wherein a diameter of the proximal portion is between about two and three times an external diameter of the neck portion.

5. The sonotrode as claimed in claim 1, wherein a ratio between an internal diameter and an outer diameter of the neck portion is between about 1:4 and 1:2.

6. The sonotrode as claimed in claim 5, wherein the internal diameter is between 50% and 80% of the outer diameter of the neck portion.

7. The sonotrode as claimed in claim 1, wherein the neck portion and the bore in the neck portion are of circular cross section.

8. The sonotrode as claimed in claim 1, wherein a ratio between a diameter of the foot portion and an outer diameter of the neck portion is at least about 3:2.

9. The sonotrode as claimed in claim 1, wherein the sonotrode is made of aluminium or an aluminium alloy.

10. An apparatus for transdermal delivery of a therapeutic or cosmetic compound, comprising an ultrasound generator, a sonotrode as claimed in claim 1 connected to the ultrasound generator, and a perforator configured to form a series of perforation passageways in the substrate into which the compound is to be delivered either prior to or during application of ultrasound.

11. The apparatus as claimed in claim 10, in which the perforator is is configured to form the series of perforation passageways by application of electromagnetic radiation to the substrate.

12. The apparatus as claimed in claim 11, in which the electromagnetic radiation is laser light or radio frequency radiation.

13. A method for transdermal delivery of one or more therapeutic or cosmetic compounds to a human or animal body, the method comprising dermal application of the compound followed by dermal application of ultrasound, wherein the ultrasound is applied via a sonotrode as claimed in claim 1 when coupled to an ultrasound transducer.

14. The method according to claim 13, wherein a frequency of the ultrasound is matched to a material and dimensions of the sonotrode such that a maximum intensity is reached between 0.3 mm and 2.0 mm below an outer surface of the skin of the human or animal body.

15. The method of claim 13, wherein the sonotrode is used in combination with iontophoresis, electroporation, magnetic force fields, electromagnetic energy, mechanical pressure fields or electrical fields.

* * * * *